US00PP20818P3

(12) United States Plant Patent
Álamo et al.

(10) Patent No.: US PP20,818 P3
(45) Date of Patent: Mar. 9, 2010

(54) BLUEBERRY PLANT NAMED 'LUCIA'

(50) Latin Name: ***Vaccinium corymbosum* L.**
Varietal Denomination: Lucia

(75) Inventors: Antonio Abad Álamo, Huelva (ES); José Ulf Hayler López, Huelva (ES); Paul M. Lyrene, Micanopy, FL (US)

(73) Assignee: Royal Berries S.L., Almonte (ES)

( * ) Notice: Subject to any disclaimer, the term of this patent is extended or adjusted under 35 U.S.C. 154(b) by 0 days.

(21) Appl. No.: 12/232,810

(22) Filed: Sep. 24, 2008

(65) Prior Publication Data

US 2009/0210977 P1 Aug. 20, 2009

(30) Foreign Application Priority Data

Feb. 14, 2008 (EP) ..... 20080341

(51) Int. Cl.
*A01H 5/00* (2006.01)

(52) U.S. Cl. ..... Plt./157

(58) Field of Classification Search ..... Plt./157
See application file for complete search history.

(56) References Cited

U.S. PATENT DOCUMENTS

PP10,675 P * 11/1998 Lyrene ..... Plt./157
PP10,788 P * 2/1999 Lyrene ..... Plt./157
PP11,033 P * 8/1999 Lyrene ..... Plt./157
PP12,783 P2 * 7/2002 Lyrene ..... Plt./157

OTHER PUBLICATIONS

UPOV ROM GTITM Computer Database, GTI Jouve Retrieval Software 2009/03 Citations for 'Lucia'.*

* cited by examiner

*Primary Examiner*—Wendy C Haas
(74) *Attorney, Agent, or Firm*—Buchanan Ingersoll & Rooney PC

(57) ABSTRACT

A new and distinct Blueberry cultivar is provided that is the product of a controlled breeding program followed by selection. The cultivar flowers and fruits at late-season. Attractive firm light blue berries are formed which exhibit an excellent sweet flavor. The plant is not self-fertile, and displays a vase-shaped growth habit with deciduous foliage. Cross-pollination is required. A low chilling requirement also is exhibited. No special sensitivity to common blueberry diseases has been encountered during observations to date. The new cultivar is well adapted for growing in well-drained soils outside tunnels.

5 Drawing Sheets

Botanical/commercial classification: *Vaccinium corymbosum* L./Blueberry Plant.
Varietal denomination: cv. Lucia.

SUMMARY OF THE INVENTION

The new Blueberry cultivar of the present invention was the product of controlled artificial pollination carried out in a greenhouse at Greenwood, Fla., U.S.A., wherein two parents were crossed which previously had been studied in the hope that they would contribute the desired characteristics. The female parent (i.e., the seed parent) was the unreleased 'FL 98-325' cultivar (non-patented in the United States). The male parent (i.e., pollen parent) was the unreleased 'FL 96-102' cultivar. The parentage of the new cultivar can be summarized as follows:

'FL 98-325'×'FL 96-102'.

The seeds resulting from the pollination were shipped to Almonte, Huelva, Spain, where they sown during approximately 2000, small plants were obtained which were physically and biologically different from each other, and selective research of the progeny was carried out. Selective study during the Spring of 2003 resulted in the identification of a single plant of the new cultivar. Initially the plant was designated S03-60-01.

It was found that the new Blueberry plant of the present invention displays the following combination of characteristics:

(a) flowers and fruits at late-season,
(b) displays a vase-shaped growth habit and defoliates during the winter,
(c) is not self-fertile,
(d) displays a low chilling requirement, and
(e) forms in abundance attractive firm light blue berries that exhibit an excellent sweet flavor.

The new cultivar well meets the needs of the horticultural industry and can be grown to advantage for the commercial production of blueberries. The new cultivar has proven to be well adapted for growing in well-drained soils outside tunnels.

The new cultivar of the present invention can be distinguished from its ancestors and all other Blueberry cultivars known to its originators. When compared to the 'Sharpblue' cultivar (non-patented in the United States), the 'Sharpblue' cultivar is evergreen during the winter. When compared to the 'Star' cultivar (U.S. Plant Pat. No. 10,675), the 'Star' cultivar commonly fruits approximately two weeks earlier. When compared to the 'Windsor' cultivar (U.S. Plant Pat. No. 12,783), the 'Windsor' cultivar displays a shorter and a more rounded growth habit. When compared to the 'Bluecrisp' cultivar (U.S. Plant Pat. No. 11,033), the 'Bluecrisp' cultivar tends to be more susceptible to Rust. When compared to the 'Santa Fe' cultivar (U.S. Plant Pat. No. 10,788), the 'Santa Fe' cultivar requires a considerably longer chill requirement. When compared to the 'Biloxi' cultivar (non-patented in the United States), the 'Biloxi' cultivar tends to be more susceptible to Stem Blight.

The new cultivar was first asexually reproduced by the rooting of softwood cuttings during the summer of 2003 at Almonte, Huelva, Spain. Such asexual propagation has shown that the characteristics of the new cultivar are firmly fixed and are stably transmitted from one generation to another. Accordingly, the new cultivar asexually reproduces in a true-to-type manner.

The new cultivar has been named 'Lucia'.

BRIEF DESCRIPTION OF THE PHOTOGRAPHS

The accompanying photographs show in color as nearly true as it is reasonably possible to make the same in color illustrations of this character, typical plants and plant parts of the new cultivar. The plants had been asexually reproduced by the rooting of cuttings, and were being grown outdoors at Almonte, Huelva, Spain.

DETAILED DESCRIPTION

Figure 1:
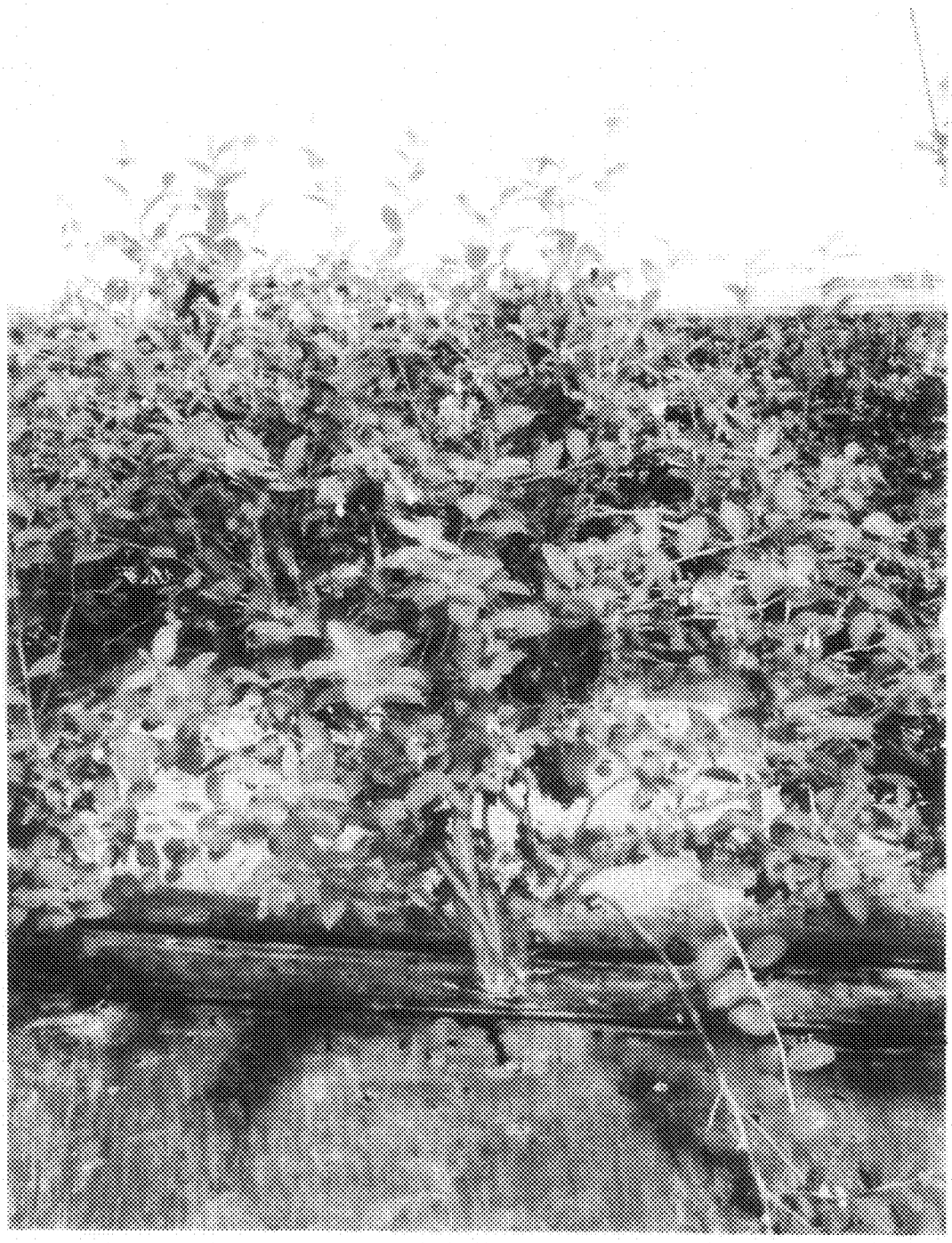
FIG. 1 shows a typical upright flowering plant of the new cultivar. The vase-shaped growth habit is apparent.
Figure 2:
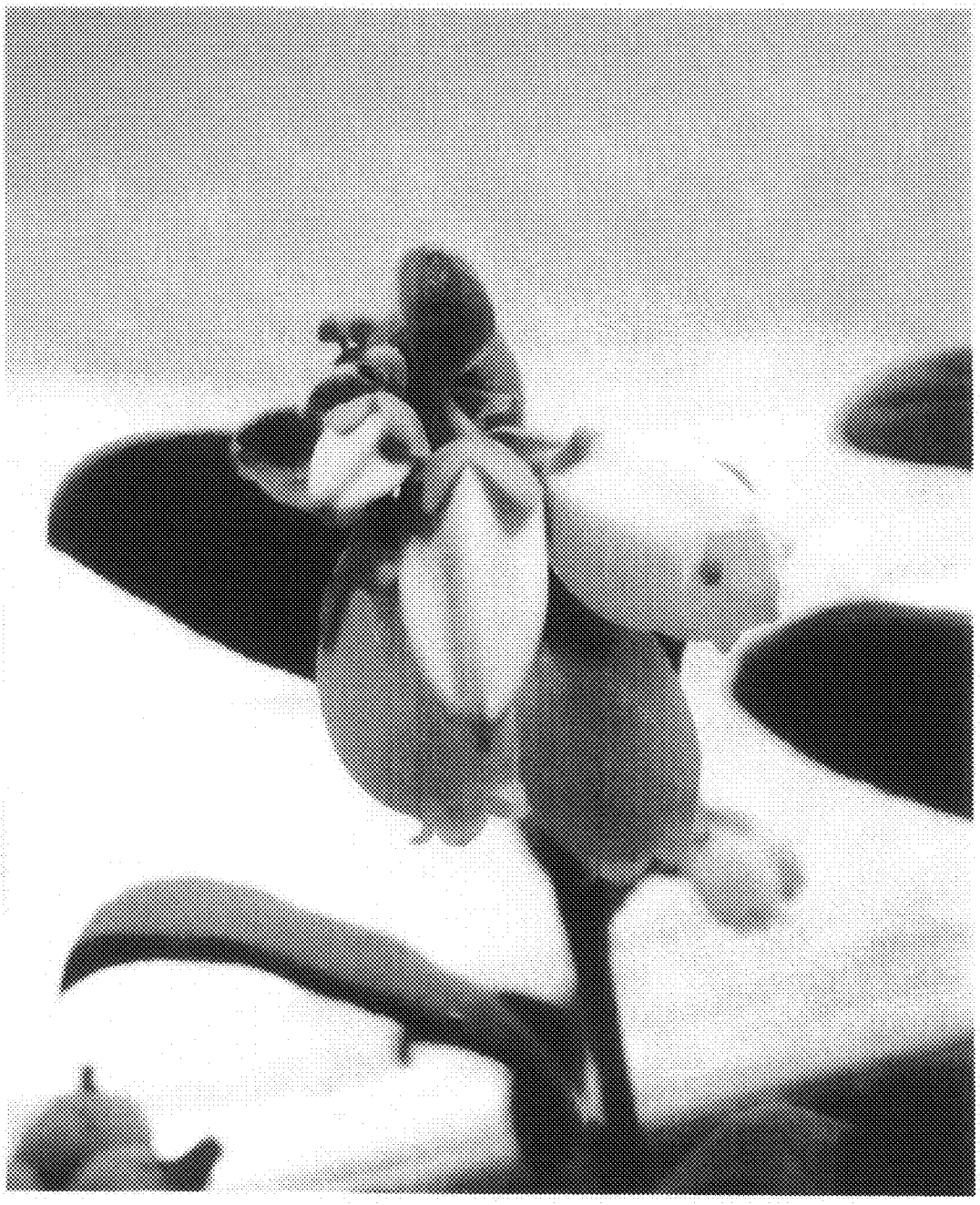
FIG. 2 shows a cluster of typical flowers of the new cultivar.
Figure 3:
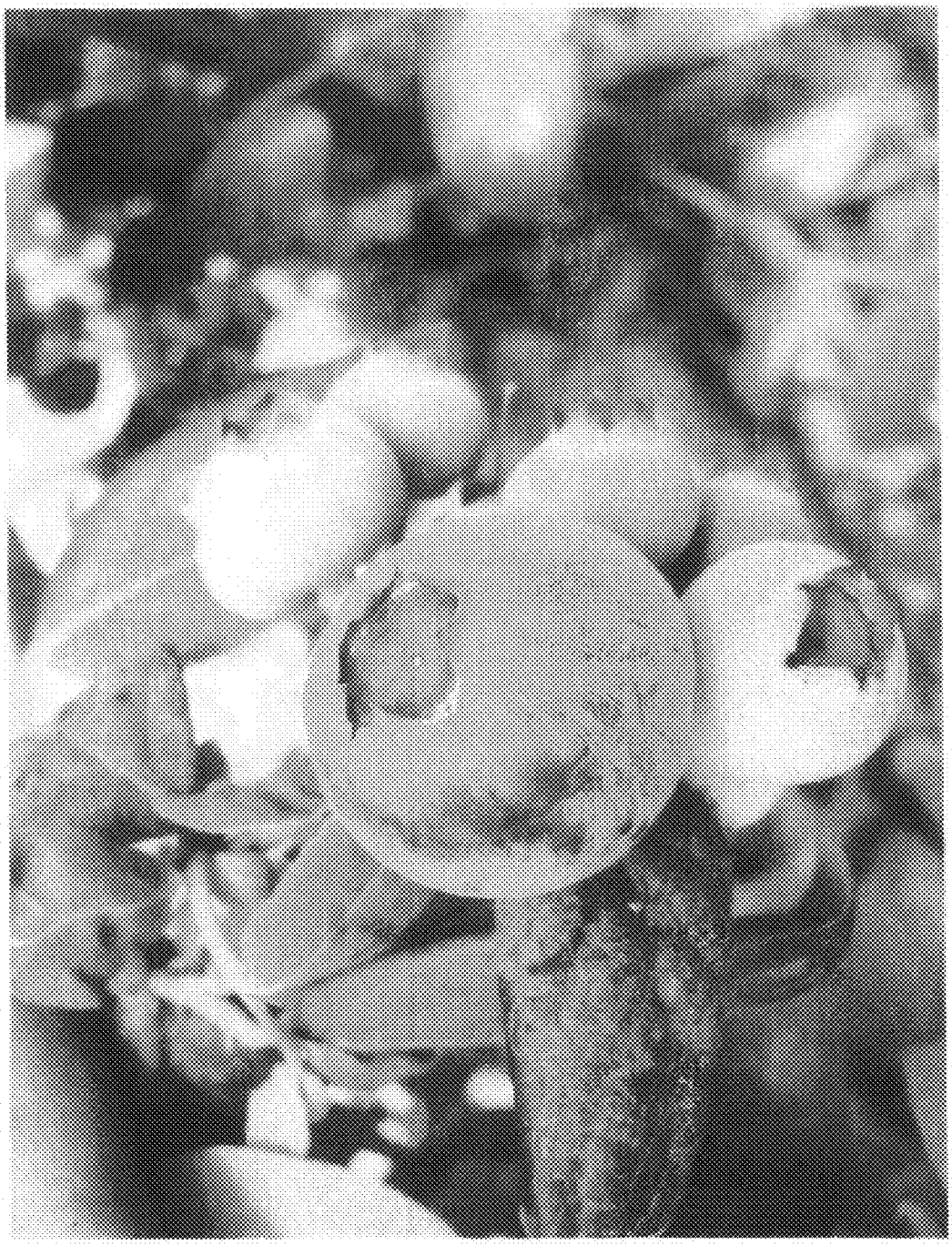
FIG. 3 shows a close view of typical berries in various stages of development of the new cultivar. A light blue mature berry is present at the center.
Figure 4:
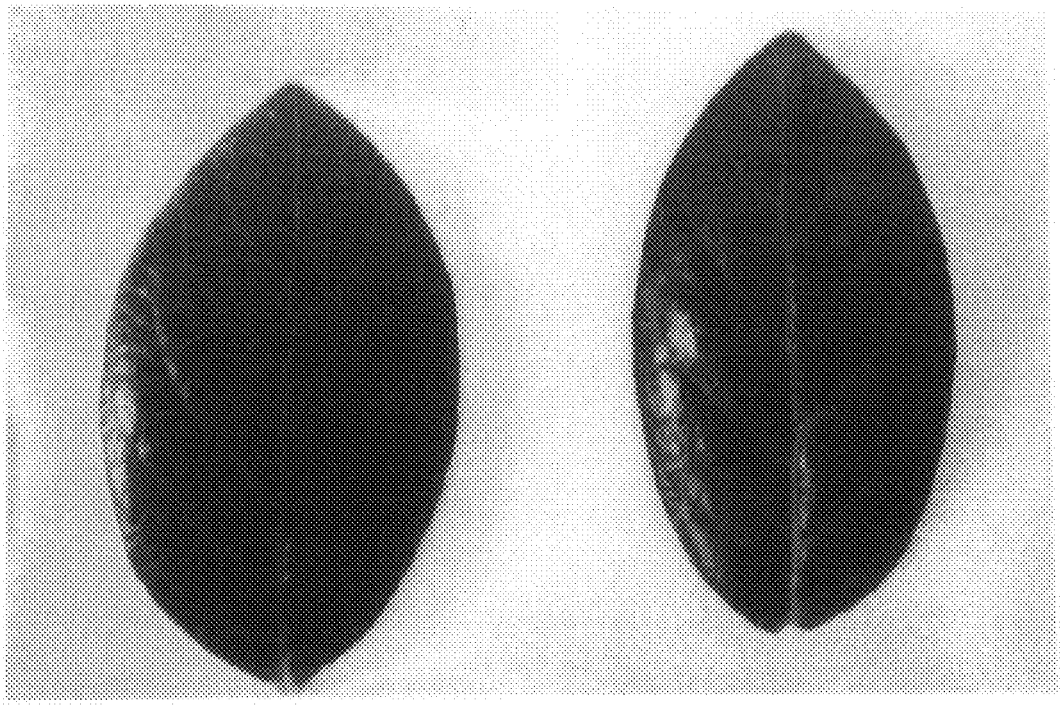
FIG. 4 shows a close view of the upper (adaxial) surfaces of a pair of typical leaves of the new cultivar.
Figure 5:
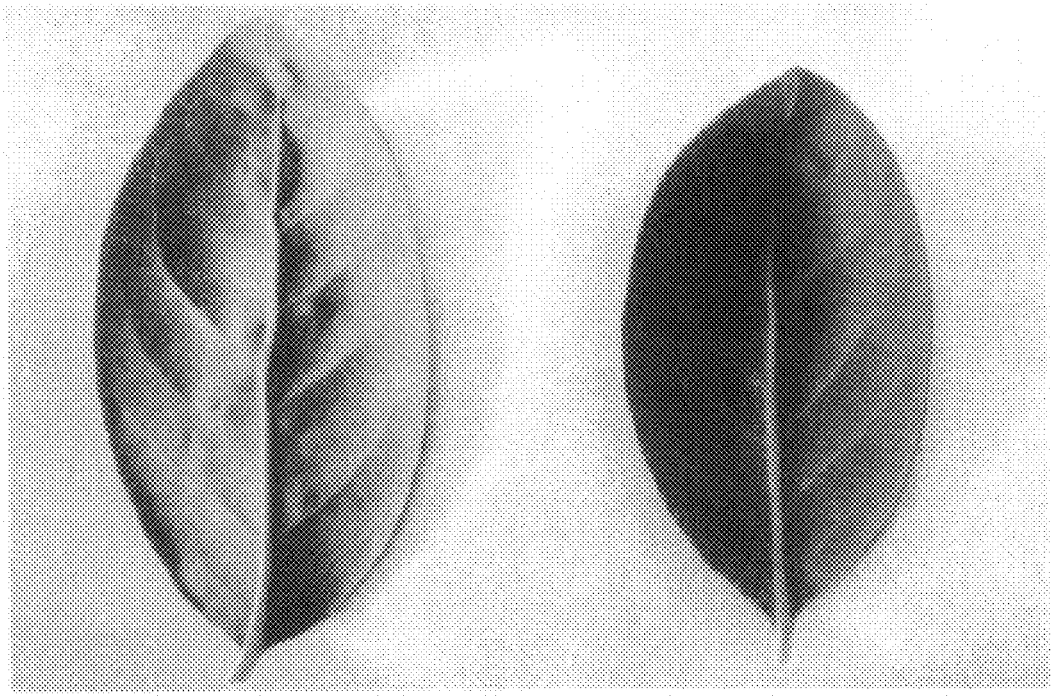
FIG. 5 shows a close view of the under (abaxial) surfaces of a pair of typical leaves of the new cultivar.
Figure 6:
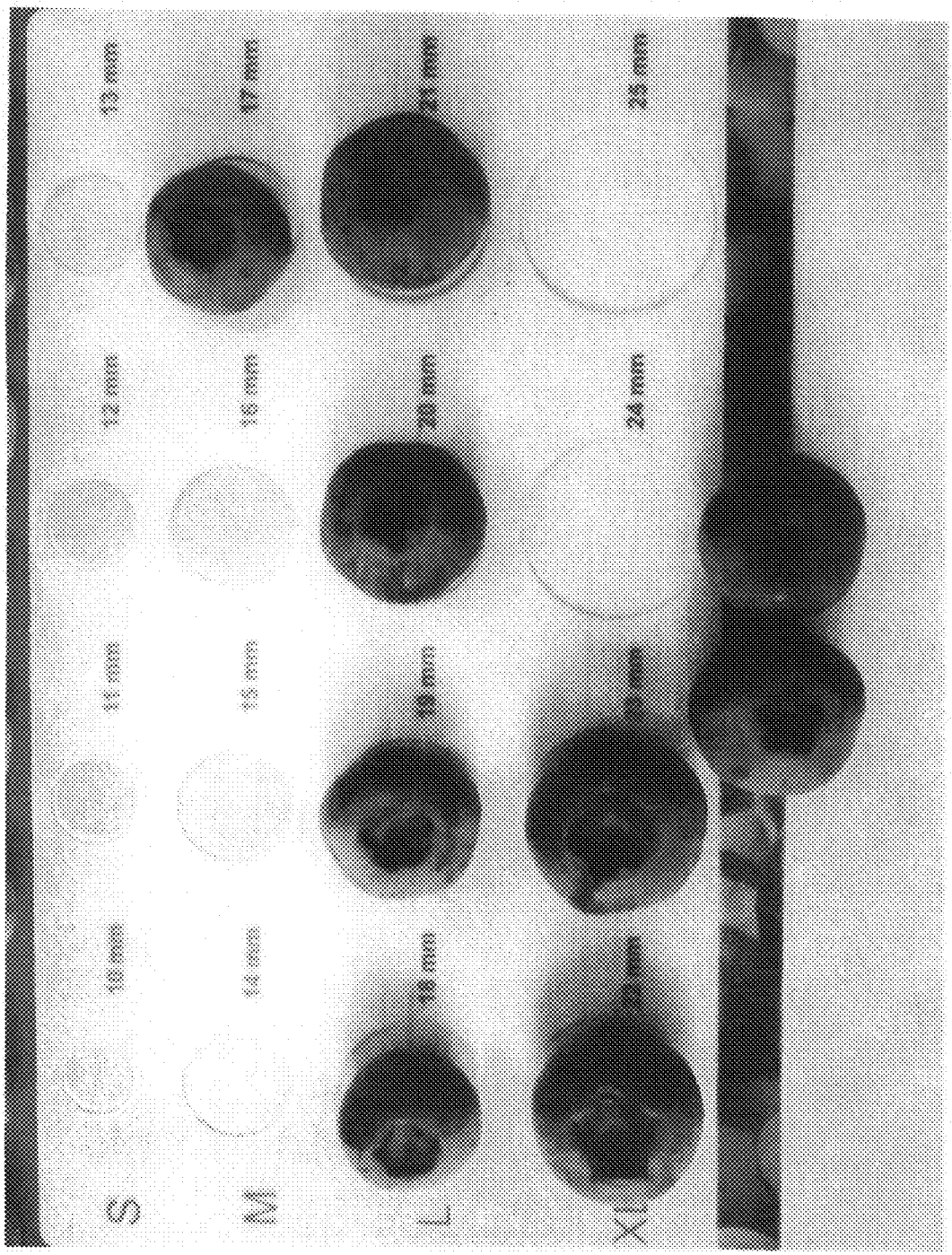
FIG. 6 shows a close view of the mature berries of the new cultivar together with a basis for size comparison.

The chart used in the identification of the colors described herein is The R.H.S. Colour Chart of The Royal Horticultural Society, London, England. Ordinary color terms are to be accorded their customary dictionary significance. The description is based on the observation while growing outdoors at Almonte, Huelva, Spain, of approximately five-year-old plants of the new cultivar which had been asexually reproduced by the rooting of cuttings.

Plant:

*Growth habit.*—Generally vase-shaped.

*Height.*—Approximately 1.4 m at 5 years of age.

*Width.*—Approximately 3.5 m at 5 years of age.

*Foliage retention.*—Deciduous, commonly with approximately 60 percent winter defoliation at Almonte, Huelva, Spain.

*Chill requirement.*—Less than 300 hours.

Foliage:

*Shape.*—Generally elliptic.

*Length.*—Commonly approximately 5.5 cm on average.

*Width.*—Commonly approximately 3.1 cm on average.

*Apex.*—Acute.

*Base.*—Acute.

*Margin.*—Entire.

*Texture.*—Glabrous and non-glandular.

*Color.*—Green Group 137A on the upper (adaxial) surface, and Green Group 138C on the under (abaxial) surface.

Flowers:

*Time.*—Late-season at Almonte, Huelva, Spain, with first flower commonly at approximately February 15$^{th}$, and 50 percent bloom at approximately February 30$^{th}$.

*Number.*—Commonly approximately 6 flowers per bud on average.

*Petals.*—5 in number and fused into a corolla tube.

*Fertility.*—Not self-fertile, cross-pollination is required.

*Fragrance.*—None.

Fruit:

*Time.*—Commonly from approximately May 10$^{th}$ to June 20$^{th}$ at Almonte, Huelva, Spain (i.e., approximately 41 days).

*Shape.*—Generally flattened and round.

*Height.*—Commonly approximately 14 mm on average.

*Width.*—Commonly approximately 20 mm on average.

*Weight.*—Approximately 3.1 g/berry on average during 2008 when plants were 4 years of age.

*Fruit scar.*—Approximately 2 mm in size on average.

*Fruit scar characteristics.*—Commonly dry and deep.

*Seed number.*—Commonly approximately 20 per berry on average.

*Seed size.*—Commonly approximately 1.6 mm in length on average and approximately 0.9 mm in width on average.

*Immature color.*—Commonly near Green Group 142D with bloom and Yellow-Green Group 145A without bloom.

*Mature color.*—Light blue, Violet-Blue Group 97B with bloom and Black Group 202A without bloom.

*Productivity.*—Approximately 3.2 Kg/plant on average during 2008 when plants were 4 years of age.

*Flavor.*—Excellent sweet flavor.

Development:

*Ability to store.*—When stored at 20° C., approximately 65 percent of the harvest commonly is good 7 days after harvest, and when stored at 8° C., approximately 100 percent of the harvest commonly is of good quality 7 days after harvest.

*Disease tolerance.*—No special sensitivity to common Blueberry diseases, such as Leaf Rust (*Pucciniastrum vacinii*), Stem Blight, and *Botrytis* Blight (*Botrytis cinerea*) has been encountered during observations to date at Almonte, Huelva, Spain. During observations to date the new cultivar has proven to be less susceptible to Rust than the 'Bluecrisp' cultivar, and less susceptible to Stem Blight then the 'Biloxi' cultivar.

*Insects.*—Is susceptible to Aphids and Thrips. During observations to date the new cultivar has proven to be more susceptible to Aphids than the 'Sharpblue' cultivar.

*Cultural conditions.*—Is well adapted for growing in well-drained soils outside tunnels.

Plants of the 'Lucia' cultivar have not been observed under all possible environmental conditions to date, Accordingly, it is possible that the phenotypic expression may vary somewhat with changes in light intensity and duration, cultural practices, and other environmental conditions without variance in the genotype.

We claim:

1. A new and distinct Blueberry plant that possess the following combination of characteristics:

(a) flowers and fruits at late-season, (b) displays a vase-shaped growth habit and defoliates during the winter, (c) is not self-fertile, (d) displays a low chilling requirement, and (e) forms in abundance attractive firm light blue berries that exhibit an excellent sweet flavor;

substantially as herein shown and described.

* * * * *